(12) United States Patent
Tumey

(10) Patent No.: US 12,404,258 B2
(45) Date of Patent: Sep. 2, 2025

(54) SYSTEM AND METHOD FOR SOLVENT-FREE CATALYZATION OF CANNABIDIOL INTO $\Delta^8$ TETRAHYDROCANNABINOL

(71) Applicant: Jonathan M. Tumey, Dayton, OH (US)

(72) Inventor: Jonathan M. Tumey, Dayton, OH (US)

(73) Assignee: Bluegrass Farmaceuticals, LLC, Miamisburg, OH (US)

( * ) Notice: Subject to any disclaimer, the term of this patent is extended or adjusted under 35 U.S.C. 154(b) by 406 days.

(21) Appl. No.: 17/869,744

(22) Filed: Jul. 20, 2022

(65) Prior Publication Data

US 2023/0021578 A1    Jan. 26, 2023

Related U.S. Application Data

(60) Provisional application No. 63/225,411, filed on Jul. 23, 2021.

(51) Int. Cl.
    *C07D 311/80*    (2006.01)

(52) U.S. Cl.
    CPC .................. *C07D 311/80* (2013.01)

(58) Field of Classification Search
    CPC ...................................... C07D 311/80
    USPC ........................................... 549/395
    See application file for complete search history.

(56) References Cited

U.S. PATENT DOCUMENTS

| 7,399,872 | B2 | 7/2008 | Webster |
| 2004/0143126 | A1 | 7/2004 | Webster et al. |

*Primary Examiner* — Taylor V Oh
(74) *Attorney, Agent, or Firm* — R. William Graham; A Patent Lawyer, LLC

(57) ABSTRACT

A solvent-free method of catalyzing cannabidiol (CBD) to a tetrahydrocannabinol (THC) utilizes a catalyst and carrier oil in combination with extraction techniques to significantly reduce cost and provide high-purity $\Delta^8$-THC. Using a non-volatile carrier oil in lieu of a highly-flammable, volatile organic solvent provides a simple process that can be incorporated into an appliance-like device that permits the safe production of $\Delta^8$-THC by a typical user in a home environment without the need for complex laboratory apparatus and expensive safety equipment.

18 Claims, 3 Drawing Sheets

SYSTEM AND METHOD FOR SOLVENT-FREE CATALYZATION OF CANNABIDIOL INTO $\Delta^8$ TETRAHYDROCANNABINOL

FIELD OF THE INVENTION

The present general inventive concept relates to an in-home system and method for producing $\Delta^8$ Tetrahydrocannabinol ($\Delta^8$-THC) utilizing a solvent-free catalyzation of Cannabidiol (CBD).

BACKGROUND OF THE INVENTION

*Cannabis* extracts are an important part of the rapidly growing marijuana industry, particularly for legal recreational use. Generally, two classes of cannabis substances receive the most attention namely, cannabinoids and terpenes. Over a hundred cannabinoids have been isolated from the cannabis plant, and these molecules range in weight from 250 to 350 amu (atomic mass units). Their physical form can be liquid or solid and contain a variety of functional groups and are non-volatile.

The essential oil of cannabis, which is a concentrate of all the active pharmaceutical ingredients in the marijuana plant, is a dynamic substance that can be transformed into numerous forms for user consumption. Extracts can be converted into tinctures, transdermal patches, effervescent tablets, drink powders, suppositories and oral tablets, vaporizing and dabbing oils.

A variety of suitable solvents are available for extracting the active ingredients from cannabis—each of which has strengths, weaknesses, laboratory infrastructure requirements and production-scaling considerations. Various methods exist for processing cannabis to extract these materials including $CO_2$ and solvent techniques which currently take significant amounts of time, complex apparatus and operator skill. Further, winterization (term coined to mean removal of unwanted wax and lipid components) is a process wherein extract is placed in a solvent, such as ethanol, and cooled to precipitate waxes and lipids which are subsequently filtered off. Thereafter, the ethanol is distilled off.

Systems that utilize carbon dioxide ($CO_2$) pressurize the $CO_2$ to its supercritical state. This converts $CO_2$ into a variably-polar solvent that passes through a chamber containing cannabis material. The filtrate can be isolated easily by reducing the pressure and evaporating the $CO_2$, leaving a cannabis extract with no solvent residue. Temperature control of these components is crucial to the operation of the process.

Another system employs a liquid hydrocarbon (pressurized butane, propane or other low molecular weight hydrocarbons in a liquid state) to pass through a bed of cannabis material and a filter, yielding an extract solution of hydrocarbon and plant extract. Similarly to $CO_2$ processing removal of processed material is performed here by a reduction in pressure which evaporates the hydrocarbon liquid, yielding a solvent-free plant extract. This method requires great attention to safety due to the flammability and hazards of fume inhalation associated with the hydrocarbon(s) used. Maintaining the pressurized hydrocarbon in the liquid state requires low temperatures. Recirculating temperature control units that can provide cooling to −60° C. (−76° F.) and below, facilitate this process. Heating circulators are also incorporated to increase the liquid hydrocarbon evaporation to isolate the extract and recycle the hydrocarbon. It is critical that cooling and heating power supply of the liquid temperature control circulators meet the capacity requirements for the size of the application.

Food grade ethanol is most commonly used as a solvent to extract plant material. Typically, ethanol is chilled to <−20° C. (−4° F.) either in a cold room or freezer and then pumped into a container of cannabis. After a soak period, the ethanol solution is either filtered or the plant material removed in a 'tea bag' fashion. The resultant mother liquor of ethanol and extract is then concentrated by removing the ethanol. Typical distillation apparatus used to remove the ethanol include rotary evaporators or a vacuum distillation system. If a jacketed vessel or jacketed filter reactor is used to cool ethanol for the extraction process, a recirculating chiller acts as the cooling source.

These extraction techniques yield oil once the solvent is removed. This oil contains plant lipids, possibly chlorophyll, waxes, fats, terpenes, CBD, CBG, CBC, THC and other cannabinoids. Additional processing to remove the plant lipids and waxes is necessary to produce a more desirable extract product and as discussed winterization is typically employed. Also, rotary evaporation techniques are employed to remove solvents.

In connection with the process, the desired input provided includes varieties of cannabis having a high content of delta-9-unsaturation-($\Delta^9$)-tetrahydrocannabinol ($\Delta^9$-THC), which is a psychoactive ingredient of marijuana whereas industrial hemp refers to varieties of the cannabis plant that have a low content of $\Delta^9$-THC. A primary intoxicating ingredient in cannabis is $\Delta^9$-THC. The most notable comparison is with cannabidiol (CBD), which is the second most abundant cannabinoid found in the cannabis plant. CBD is often arguably touted as "non-psychoactive."

Hailed for its natural anecdotal anti-inflammatory and pain-relieving properties, CBD is being added to everything from skincare to food. It has many known benefits, including, treatment of migraines, aches, pains, nausea and vomiting, glaucoma, Parkinson's disease, Huntington's disease, anxiety, epilepsy and Alzheimer's disease. $\Delta^9$-THC is only one of a family of about 60 bi- and tri-cyclic compounds named cannabinoids. For example, delta-8-unsaturation $\Delta^8$-THC is a double bond isomer of $\Delta^9$-THC and is a minor constituent of most varieties of cannabis.

The major chemical difference between the two compounds is that $\Delta^9$-THC is easily oxidized to cannabinol whereas $\Delta^8$-THC does not readily oxidize and is in fact very stable. The difficulties of the synthesis are due in part to the facts that the materials are typically non-crystalline, and are often quite difficult or impossible to separate and purify without utilizing High-performance Liquid Chromatography (HPLC), the aromatic portion of the molecule is very sensitive to oxidation, particularly in the presence of base or transition metals and the $\Delta^9$-THC is thermodynamically disfavored relative to $\Delta^8$-THC. There is also no general method by which to favor $\Delta^9$-THC kinetically.

Isolation of CBD for medicinal applications requires additional processing to remove terpenes and remediate THC content. Various marijuana plant strains now produce higher amounts of CBD. Likewise, many varieties of hemp can be used as the starting material. In producing CBD, reduction in THC content is important to eliminate the psychoactive "high" effect to yield a product rich in CBD for anti-inflammatory, anti-seizure and other indications. Terpenes, THC and CBD have high boiling points (156-250° C.; 312-482° F.) and thus distillation under atmospheric conditions is undesirable and exposure to oxygen at these high temperatures can promote oxidation and prolonged heat exposure leads to thermal decomposition. By applying a vacuum, the boiling points are lowered. Vacuum conditions remove oxygen, thus eliminating product oxidation while lowering the boiling point temperature to lessen heat exposure.

A short path distillation apparatus provides the means for heating oil in a flask under vacuum (typically with a magnetically stirred hot plate) with a short path distillation attachment. The condenser is cooled with a recirculating chiller to provide cooling for condensation of the component vapors. As the vapor temperature increases, indicating a new compound/mixture fraction, a multi-position receiving flask is positioned to isolate the different fractions of terpenes, THC and CBD. Optionally, a longer fractionating column (Vigreux, Oldershaw, etc.) can be installed between the vessel with heated oil and the condenser apparatus enabling finer separation of the components. These processes are time consuming in the effort to derive the various fractional components.

As noted in Webster, U.S. Pat. No. 7,399,872, $\Delta^9$-THC and to a lesser degree, $\Delta^8$-THC were a focus of production. Prior art discussed therein namely, Gaoni and Mechoulam (1966, Tetrahedron 22: 1481-1488), report converting cannabidiol (CBD) to, among other compounds, $\Delta^8$-THC and $\Delta^9$-THC comprising boiling a solution of CBD (3.0 g) in absolute ethanol (100 ml) containing 0.05% HCl for 18 hours. The solution was then poured into water and extracted with ether. The ether solution was washed with water, dried ($Na_2SO_4$) and evaporated. $\Delta^8$-THC and $\Delta^9$-THC were eluted from the resulting oil and separated by chromatography. In another experiment, CBD (3.14 g) was dissolved in benzene (100 ml) containing 2 mg/ml p-toluenesulphonic acid and boiled for two hours. The reaction mixture was poured into water and the upper layer was separated, washed with 5% $NaHCO_3$, then with water, dried and evaporated. Elution with pentane-ether (95:5) gave an oily material which was subsequently distilled. Percentage yield of $\Delta^8$-THC ($\Delta^{1(6)}$-THC) was given as 64% of the crude material in this paper. The crude oil product, which showed only one spot by thin layer chromatography, was purified by vacuum distillation.

Gaoni and Mechoulam (1964, J Amer Chem Soc 86: 1646) also described a method for converting CBD to $\Delta^9$-THC comprising boiling a mixture of CBD in ethanol containing 0.05% hydrogen chloride for 2 hours. Percentage yield of $\Delta^9$-THC ($\Delta^1$-THC) was 2% (Mechoulam et al, 1972, J Amer Chem Soc 94: 6159-6165; Mechoulam and Gaoni, 1965, J Amer Chem Soc 87: 3273). Using boron trifluoride, the yield was 70% (Gaoni and Mechoulam, 1971, J Amer Chem Soc 93: 217-224) although purity was not given.

Webster describes a method of converting CBD to a tetrahydrocannabinol which includes providing a reaction mixture comprising a catalyst in an organic solvent, adding CBD to the reaction mixture, mixing the reaction mixture, allowing the mixture to separate into an aqueous phase and an organic phase, removing the organic phase, and eluting the tetrahydrocannabinol from the organic phase. To further convert CBD to $\Delta^8$-THC there is provided a reaction mixture comprising a Lewis acid in an organic solvent to which is added CBD. This is refluxed under a nitrogen atmosphere and diluted with an organic solvent. The mixture is poured into cold water and mixed allowing the mixture to separate into an aqueous phase and an organic phase where the organic phase is removed. Then, $\Delta^8$-THC is eluted from the organic phase.

Another method of converting CBD to $\Delta^9$-THC is disclosed which adds $NaHCO_3$ to the reaction mixture, and after separation eluting $\Delta^9$-THC from the organic phase. Also, disclosed is converting CBD to a tetrahydrocannabinol by providing a reaction mixture with a catalyst in an organic solvent and eluting the tetrahydrocannabinol from the organic phase and mixing the eluted tetrahydrocannabinol with a suitable excipient.

It is recognized that cannabinoids are of growing medicinal value, and improved methods of converting CBD to $\Delta^8$-THC and/or $\Delta^9$-THC are needed. A major limitation of the prior art methods is the requirement that a volatile solvent be utilized which is a fire hazard as well as a health hazard. The employment of solvents, such as toluene, as part of the reaction requires the use of complex laboratory equipment such as a fume hood in order to carry out the conversion safely. The present general inventive concept provides an improved system and methods for processing Hemp for the catalyzation of CBD into $\Delta^8$-THC without the use of dangerous volatile solvents. Eliminating this hazard as a necessary part of the reaction makes the commercialization of a safe and easy-to-use in-home machine possible.

SUMMARY OF THE INVENTION

It is an object to improve catalyzation of CBD into $\Delta^8$-THC derived from Hemp.

It is another object to reduce cost of production of $\Delta^8$-THC.

It is an object to provide a system and method for catalyzing CBD from Hemp (*Cannabis sativa* L. w/total THC<0.3%) to produce $\Delta^8$-THC without the use of a volatile solvent.

A further object is to provide a safe, easy-to-use appliance-like device for catalyzing CBD from Hemp (*Cannabis sativa* L. w/total THC<0.3%) to produce $\Delta^8$-THC without the use of a volatile solvent and which can be safely operated in the home.

Yet another object is to provide a home-based system and method for catalyzing CBD from Hemp (*Cannabis sativa* L. w/total THC<0.3%) to produce $\Delta^8$-THC without the use of a volatile solvent, and subsequently post-processing the $\Delta^8$-THC into various consumable products including the following:

Edibles/Cookables—Mg $\Delta^8$-THC based on whatever product strength is desired (i.e., 10 mg, 100 mg)

Tinctures/Elixir/Capsules—Mg $\Delta^8$-THC based on whatever product is desired to be dissolved by carrier Topicals—Mg $\Delta^8$-THC based on whatever product strength is desired (i.e., 10 mg, 100 mg)

Dabbables—85% $\Delta^8$-THC

Vapes—65-75% $\Delta^8$-THC diluted slightly with terpenes for flavor.

DETAILED DESCRIPTION OF PREFERRED EMBODIMENTS

Figure 1:
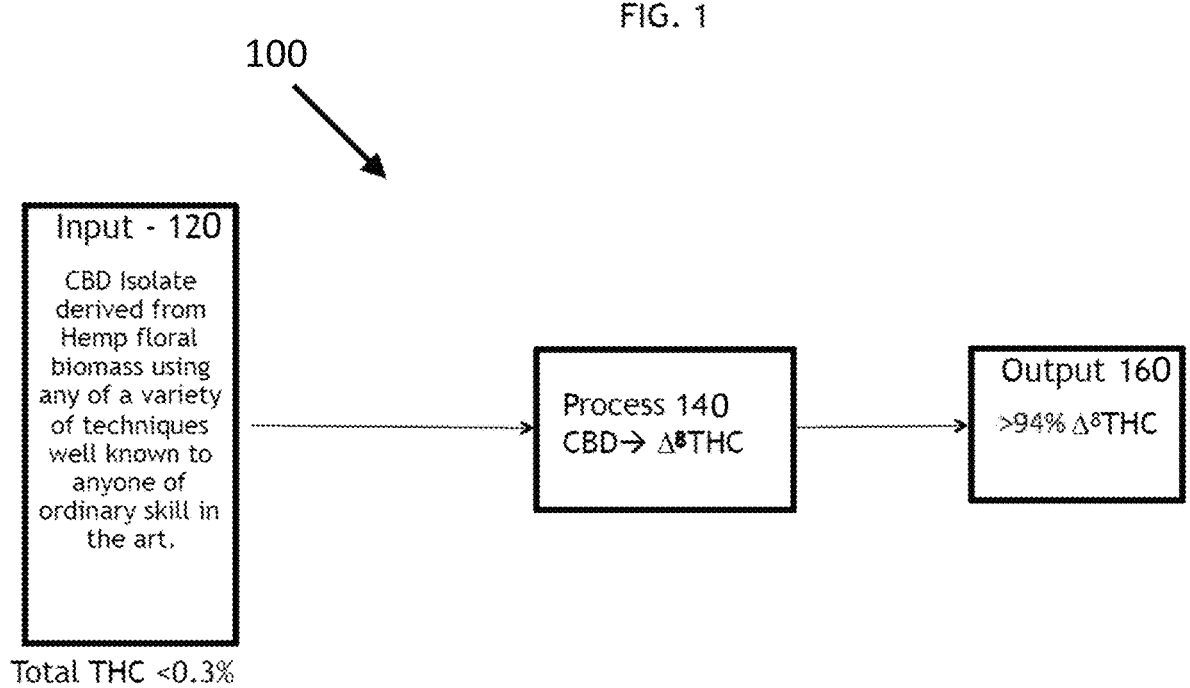
FIG. 1 is a schematic of one pathway for catalyzing CBD to $\Delta^8$-THC.

Referring now to the drawings, a system and method for solvent-free catalyzation of CBD into $\Delta^8$-THC is generally represented by the numerals 100, 200 and 300. In accordance with the present general inventive concept, cannabis plant material or cannabis biomass, which, as used herein, primarily includes chopped, crushed or ground flowers and buds, is placed into an extraction vessel and is substantially covered with a solvent. The solvent can include those known in the art, in order to obtain the CBD which is to be further processed in the instant general inventive concept.

Solvents utilized in processing the cannabis biomass could also include dichloromethane, ethanol or toluene, and $CO_2$ for example. Other potential solvents include: Tetrahydrofuran (THF), Ethyl acetate, Acetone, Dimethylformamide (DMF), Acetonitrile (MeCN), Dimethyl sulfoxide (DMSO), Nitromethane, Propylene carbonate, Formic acid, n-Butanol, Isopropyl alcohol, n-Propanol, Methanol, Acetic Acid and Water.

Figure 2:
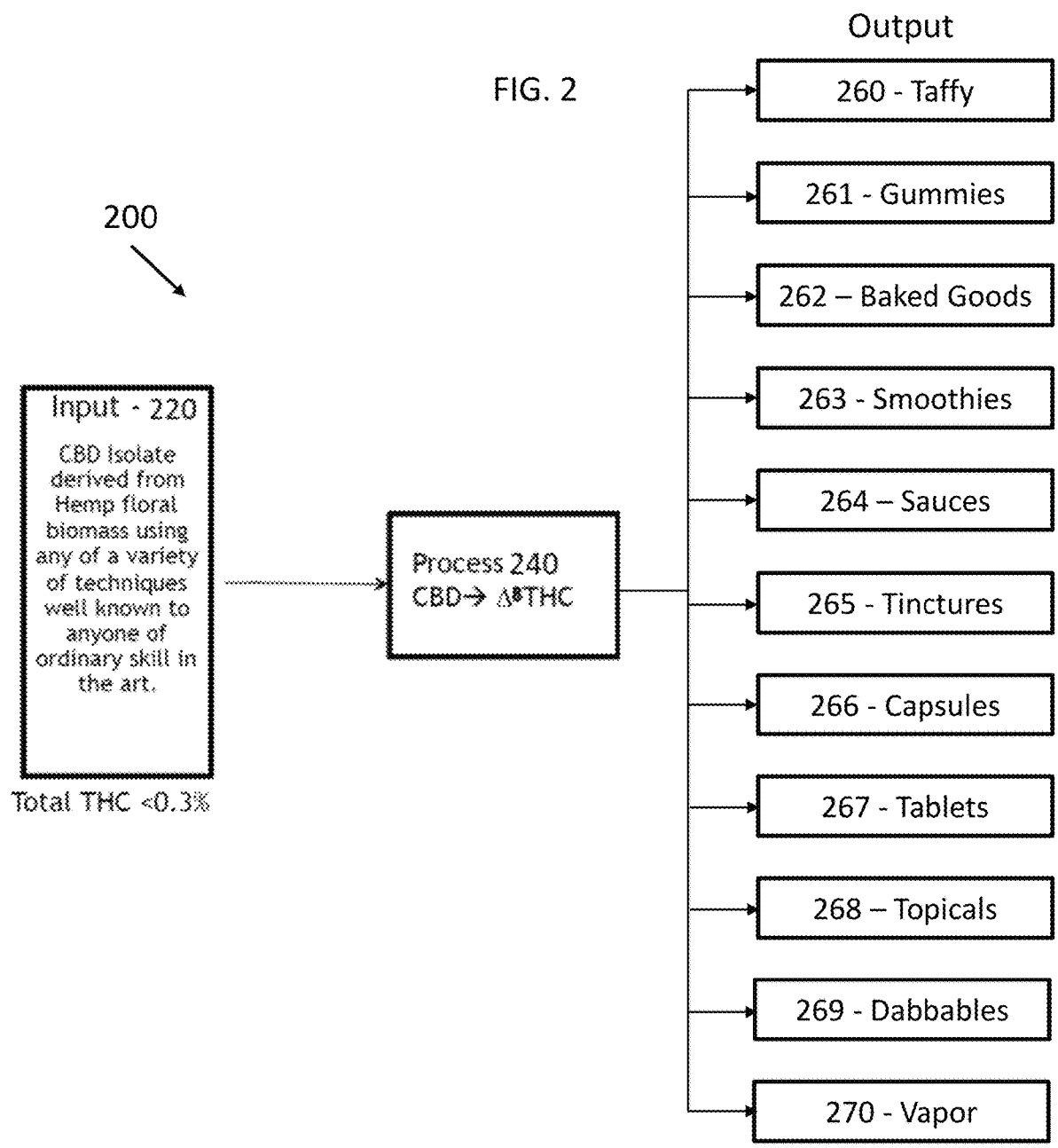
FIG. 2 is a schematic of another pathway for catalyzing CBD to $\Delta^8$-THC and subsequently preparing compositions for personal consumption.

An exemplary process as shown in FIGS. 1-2, provides for an input 120, and 220, wherein the input 120, for example, CBD isolated derived from hemp is utilized in conjunction with process 140 in accordance with Example 1 of the present general inventive concepts comprises a solvent-free method to produce an output 160 of >94% $\Delta^8$-THC with minimal $\Delta^9$-THC as seen in FIG. 1. Similarly, input 220 as will be seen from the Example 2 herein, wherein like process 240 is employed to produce an output 260 of >94% $\Delta^8$-THC with minimal $\Delta^9$-THC that is subsequently utilized in the preparation of myriad output compositions in accordance with Exemplars 260 through 270 for personal consumption.

Unless defined otherwise, all technical and scientific terms used herein have the same meaning as commonly understood by one of ordinary skill in the art to which the present general inventive concept belongs. Although any methods and materials similar or equivalent to those described herein can be used in the practice or testing of the present invention, the preferred methods and materials are now described. All publications mentioned hereunder are incorporated herein by reference.

Definitions

As used herein, CBD refers to Cannabidiol.
As used herein, $\Delta^8$-THC refers to $\Delta^8$-tetrahydrocannabinol.
As used herein, $\Delta^9$-THC refers to $\Delta^9$-tetrahydrocannabinol.
As used herein, CBN refers to Cannabinol.
As used herein, MCT refers to Medium Chain Triglycerides.
As used herein, HPLC refers to High Performance Liquid Chromatography.
As used herein, GC-MS refers to Gas Chromatography—Mass Spectroscopy.
As used herein, FID-GC refers to Flame Ionization Detector—Gas Chromatography.

As will be appreciated by one knowledgeable in the art and as discussed below, the reaction times may be varied somewhat, producing product at different yields and purities. Furthermore, functional equivalents may be substituted where appropriate.

As discussed below, yield is determined by looking at the peak area for the isolated compound in the gas chromatography—mass spectra analysis of the crude reaction product mixture. It is important to note that in the prior art, yield is often calculated on the basis of first isolated crude product before final purification.

In some embodiments of the process, as discussed below, yield is at least 90%. Purity is also determined by GC-MS and also by analytical HPLC. The total ion chromatogram from the GC-MS gives information similar to that provided by an FID-GC in that the peak area is proportional to the mass of the analytes detected. Total peak area and the peak areas of the individual analytes can be compared in the GC-MS case as long as the masses are in generally the same range. As discussed below, in some embodiments, purity of the tetrahydrocannabinols isolated by the process is greater than 90%. Importantly, these results are achieved at significantly lower cost and with more efficiency. The invention provides a series of preferred steps in the conversion of cannabidiol.

The present general inventive concept will now be described by means of examples, although the present inventive concept is not limited to these examples.

Example 1 as Illustrated in FIG. 1

Detailed Process Disclosure Pathway I (CBD Isolate to $\Delta^8$-THC)

1. The initial process is to obtain and validate pure CBD isolate from *Cannabis sativa* L. "Hemp" using various techniques well known to anyone of ordinary skill in the art. The purity of isolate was at least 98% CBD.
   a. Ideal Cannabinoids and Cannabinoid limits are as follows:
      i. CBD≥98%
      ii. Sum of $\Delta^9$-THC, $\Delta^8$-THC, THCA & THCV≤0.3%
      iii. Cannabinoids CBG, CBC, CBN should be in the range of: 0.01-1.7%
      iv. Cannabinoids (CBDV, CBDA, CBGA) should not exceed 1.5%
      v. Sum of any unidentified cannabinoids should not exceed 0.5%. (Note, additional cannabinoids or cannabinoid levels that exceed the reported levels would be detrimental to the overall reaction efficiency.)
2. Isolate preparation: The isolate is refrigerated at temperatures ranging from 0-10° C. to prevent degradation thereof, and weighed prior to the reaction and molar calculation is performed, wherein the catalyst below is generated based on a fraction of the molarity of CBD isolate input material.
3. Catalyst preparation: The catalyst consists of two components, organic food grade oils and a catalytic reagent. The food grade oil used in this example is MCT oil. These can be mixed in varying amounts to account for different reaction scales in terms of how much isolate is going to be utilized in the reaction.
   a. Organic food grade oils are used to solubilize the catalytic reagent
      i. A calculated quantity of catalytic reagent is added to a known volume of food grade oil and is stirred to produce a catalytic slurry.
   b. The catalyst can preferably be para-toluenesulfonic acid (PTSA), lanthanide series triflate, triflates, or acids; in general catalyst is added based on the amount of isolate weighed using 0.0001-0.2000 mole fraction of catalyst per X moles of isolate.
   c. The MCT oil and the catalyst component are premixed in a reaction vessel, preferably a round-bottom flask, utilizing magnetic stirring (reference FIG. 3 reaction chamber 304 described in detail herein below).
4. After the catalyst is mostly/completely dissolved the CBD isolate can be slowly added to the mixture at a rate of about 5 g/min.

5. After CBD isolate for the batch has been charged into the catalytic slurry contained in the reaction vessel, the contents are stirred and heated for a period of preferably 2 hours.
   a. Product reaction parameters are as follows:
      i. Temperature Range: −20° C.-111° C. (dependent on application);
      ii. Stir Speed is set to 0 to 3000 RPM (optimum stir speed dependent on application); and
      iii. Reaction Time Ranges vary from 0.5 h-24 h (dependent on application)
6. After the reaction time has transpired the contents of the reaction vessel are emptied and rinsed with a specific volume of cold water to quench the $\Delta^8$-THC Catalyst mixture.
   a. The contents of the reaction vessel and a predetermined volume of cold water are vigorously stirred for preferably 15 minutes.
      a. Brine is preferably added in small aliquots while stirring.
      b. The quenched and brined mixture is then added to a separatory funnel for separation into aqueous and oil layers. Step 7 Details the process for Decanting and Separating the liquid-liquid matrix.
Note that for any transfers or rinses, small amounts of MCT oil and DI water are used to rinse the contents of the flask into the receiving flask or vessel.
   7. Decantation/Separation of reaction mixture
      i. After quenching and before separating, the separatory funnel is shaken vigorously and is vented three times and is allowed time for both the Oil and water layer to separate (if emulsion is present after allowing time for layers to separate, more saturated brine solution* is added and the funnel is agitated and vented up to 3 additional times) *DI water and NaCl.
      ii. After clear separation has been achieved, the water layer is separated and the oil layer is poured into a stirring saturated solution of sodium bicarbonate. The water layer is extracted preferably twice more with fresh food-grade oil. The additional oil layers obtained from the additional separations are combined and added to the stirring saturated solution of sodium bicarbonate containing the first and most concentrated oil layer.
      iii. The combined oil layers and saturated sodium bicarbonate solution is magnetically stirred for preferably 15 minutes. The mixture is vigorously agitated while venting three times. The emulsions are allowed to settle and the layers to fully separate.
      iv. After complete separation is visible and apparent, the sodium bicarbonate wash layer is removed and the oil layer is added to a clean storage jar.
         a. If there are water droplets present in the oil a small amount of drying agent such as anhydrous magnesium sulfate or sodium sulfite can be added and stirred into the mixture. After stirring, filter via gravity, vacuum or syringe to remove the drying agent from the high purity oil.
      v. The high purity oil layer contained in the dry beaker is ready for consumption can be used to create any of the variety of products disclosed in FIG. 2.
         1. Oil At this stage contains about 94% $\Delta^8$-THC and MCT oil.
            a. The strength or dosage of the high purity oil can be estimated and calculated by:
               i. Determining how MCT was added to the volume throughout the process.
               ii. Determining how much CBD isolate was input as starting material.
               iii. This information will provide a mg/ml concentration
                  1. The amount of $\Delta^8$-THC present (in grams) in the MCT oil at the end of the process will be equal to about 85% the mass of the input CBD used in the process.

Example 2 as Illustrated in FIG. 2

Detailed Process Disclosure Pathway II (CBD Isolate to $\Delta^8$-THC and Subsequently $\Delta^8$-THC Consumables)
Steps 1-8 are the same as described in Example 1 above.
   9. Sequester product source material. At this point the material generated by the above steps is highly pure $\Delta^8$-THC infused in a carrier oil with minor impurities, notably $\Delta^9$-THC, THC isomers, CBD and CBN. The material exists as $\Delta^8$-THC in a predetermined quantity of carrier oil and can subsequently be processed into one of many products using the following Exemplar techniques. (NOTE: this is the raw material which can be post-processed into consumable end-products such as comestibles, etc.)
   10. Preparing $\Delta^8$-THC Comestibles:
      a. Exemplar 260—Taffy
         i. In a saucepan, homogenize mixture of sugar and cornstarch.
         ii. To the homogenized mix add corn syrup, water, butter and salt.
         iii. Further mix to homogenize newly added ingredients, gently begin warming the candy mixture.
            1. Bring the mixture to a boil and raise the temperature until it reaches 250° F.-265° F. (121° C.-129° C.) [hard ball stage]
         iv. After the candy mixture has achieved hard ball stage, immediately remove from heat source and stir in flavoring, citric acid and potassium sorbate solution followed by a pre-determined volume of high-purity oil.
            1. Flavoring can be artificially or naturally derived
               a. Powdered drink mixes are used in this example
               b. Juices and liquid flavor bases can be used as well
            2. Preservatives (citric acid, potassium sorbate) or other food industry standard approved food preservatives by be utilized to prolong shelf life of the end-product.
            3. High-purity $\Delta^8$-THC infused-oil amount dependent on target dosage but can be directly added along with the other ingredients of this step.
         v. After addition of flavoring, preservatives and high-purity oil, vigorously stir the mixture for 5-10 minutes or until completely homogenized.
         vi. Once thoroughly mixed, pour the warm candy mixture onto sheet pan(s) coated with a thin layer high-purity oil.
         vii. Let the candy cool to the point where it can be handled and manipulated.
         viii. Use high-purity oil to coat hands and begin pulling the candy until it lightens in color and becomes firmer.
         ix. Roll the pulled taffy into an evenly distributed cylinder on a sheet pan or long strip of wax paper and then cut into bite-sized pieces.

1. Pieces can be easily cut using scissors or a knife that has been lubricated with high-purity oil.
2. Individually wrap cut pieces in squares of wax paper to preserve for future consumption.

b. Exemplar 261—Gummies
   i. Add one box of flavored gelatin and one packet of unflavored gelatin with a ¼ teaspoon of citric acid and homogenize the mixture with a whisk.
   ii. To the starting materials add, ⅓ cup water, ¼ cup corn syrup and ⅓ tablespoon potassium sorbate solution and homogenize gently as to not introduce air bubbles into the mixture.
   iii. After mixing, allow the gelatin to bloom by letting it sit for 10 minutes.
   iv. Once bloomed, heat the gummy mixture gently with a heating element/surface or by microwaving the mixture.
      1. Do not exceed boiling temperature 212° F. (100° C.) and heat for 30 seconds.
   v. At this stage add the high-purity oil and gently mix to ensure complete homogenization.
   vi. Heat the mixture again for 15 seconds and stir for 10 seconds and repeat this step for a total of 3 times.
   vii. Permit the gelatin cool for 10 minutes, checking every 150 seconds to agitate/stir for a total of 4 cycles.
   viii. Prepare gummy molds with commercially available cooking spray/oil.
   ix. Using a turkey baster or syringe fill each cavity of the gummy molds nearly to the top without over filling.
      1. If the mixture becomes difficult to transfer it can be gently warmed, stirred and pipetted into the remaining cavities of the gummy molds.
   x. Cool gummy molds in the refrigerator for 30 minutes.
   xi. Remove the gummies from the molds after cooling and spread them out on a wax paper sheet to dehydrate.
      1. Expedited dehydration can be accomplished using a commercially available dehydrator oven, well known in the art.
         a. The dehydrating method with the oven consists of a 24-hour drying period followed by a sugar-coating process and another 24-hour drying period and final sugar-coating process.
            i. Dehydration temperature is set to 95° F. (35° C.).
      2. The conventional and natural dehydration method consists of a total of 72 hours open air dehydrating.
   xii. After the first 24 hours the gummies are coated with a sugar coating and are dehydrated for another 24 hours before a second application of sugar coating.
   xiii. After the second coating has been applied the gummies can sit for 24 more hours at room temperature.
      1. Sugar coating consists of adding a predetermined ratio of sugar to citric acid.
         a. Citric acid acts as a preservative and souring agent, add more citric acid for a sourer taste.
         b. Citric acid also pulls out moisture from the gummies which improves shelf-life and reduces dehydration time.
         c. It is crucial that the gummies are sugar coated intermittently during the dehydration process to reduce moisture to a higher degree and in a shorter amount of time.
   xiv. The dehydrated and fully coated gummies can be stored in a bag or jar that has an appropriately sized desiccant packet in it.

c. Exemplar 262—Baked Goods (Including Cookies, Brownies, Cakes)
   i. Prepare high-purity oil and set measured amount to the side while preparing baked goods recipe.
   ii. Depending on the baked good the high-purity oil is added whenever the recipe calls for oil/butter to be added
      1. To make the butter for cookies, cakes and the likes start by dissolving the butter in a saucepan and by adding an amount of high-purity oil dependent on target dosage.
   iii. Homogenize the butter and oil and refrigerate until solid.
      1. At this point the butter infused with high-purity oil can be used in the recipes.
      2. Keep in mind that cannabinoids degrade at higher temperatures, to avoid degradation of cannabinoids heat the oven to 300° F. (149° C.) and do not exceed this temperature.
      3. Since the temperature is lower be sure to bake the baked goods for 10-20 minutes longer than recommended.
   iv. Check goods intermittently until they appear to be baked to completeness.

d. Exemplar 263—Smoothies/Milkshakes
   i. Prepare smoothies/milkshakes using any desired and common method, well known in the art, and add high-purity $\Delta^8$-THC infused-oil in desired amount prior to blending mixture.
      1. Can be added to existing milkshakes and smoothies as long as they can be homogenized after the addition of the high-purity oil.
      2. Bottled smoothies or blended drinks can accommodate 1 tsp-1 tbsp high-purity oil.
   ii. Add 1 tsp-1 tbsp high-purity oil and shake bottle to mix.

e. Exemplar 264—Sauces (Including Dressings)/Oils, Butter Infusions
   i. Sauces
      1. High-purity oil can be incorporated into existing sauce products or can be added to sauce recipes.
         a. Note: this method is best applied to non-aqueous based sauces.
      2. High-purity oil is incorporated into sauces by gently heating the sauce.
         a. While heating, high-purity oil is added to the mixture.
         b. The mixture is stirred vigorously for 5-15 minutes or until completely mixed.
         c. Cool the infused sauce to room temperature and store refrigerated in a sealed container.
   ii. Butters/Oils
      1. Butters and oils are infused by warming up gently and by adding high-purity oil to the mixture with generous amount of stirring.
         a. When it is completely homogenized the mixture can be transferred into a sealable container.
            i. Infused Butters are stored refrigerated.

ii. Infused Oils may be stored at room temperature.
  b. These infused starting ingredients can be used for many of the recipes disclosed.
11. Preparing Δ⁸-THC Tinctures and Tablets:
  a. Exemplar 265—Sublingual Tinctures
    i. Pour a measured amount of high-purity oil based on target dosage into a vessel.
    ii. Add required amount of MCT oil to high-purity oil and warm to just below 212° F. (100° C.) while stirring to dissolve and homogenize the ingredients.
      1. The oil can be diluted to the target dosage based on the amount of MCT oil added.
    iii. After the MCT oil and high-purity oil has been mixed, remove from heat source and add in oil soluble flavoring.
      1. Artificial or natural food flavoring may be used as long as it is an oil-soluble formula.
    iv. Once the flavoring has been added homogenize for another 5 minutes.
    v. Let the mixture cool to room temperature and then add to bottles for storage and accurate dose administration.
  b. Exemplar 266—Capsules
    i. Using commercially available gel capsules and a syringe outfitted with a blunt-tip, add the high-purity oil to one side of the capsule and seal the other end.
    ii. Store capsules in a sealed and light-proof container.
  c. Exemplar 267—Tablets
    i. Mix 1-part high-purity oil with 10 parts maltodextrose and homogenize.
    ii. Take mixture from Step i. and blend with typical tableting excipients.
      1. Excipients required are binding/tableting agents and preservatives.
        a. Binding agents can be made from glucose, sucrose and starch.
        b. Citric acid is added in small amounts to act as preservative.
    iii. Take the mixture created in Step ii. and add to a pill press.
    iv. Press until tablet is formed and store in a sealed container.
12. Preparing Δ⁸-THC Topicals:
  a. Exemplar 268—Topical Creams
    i. High-purity oil can be incorporated into existing products and can be included in most topical recipes.
      1. To incorporate into existing products, gently warm the product in an accommodating vessel.
        a. Add high-purity oil to the warmed topical and homogenize to completeness.
        b. Cool the mixture and transfer into a sealable container.
      2. When adding to DIY topical recipes, the high-purity oil may be incorporated as the final ingredient prior to homogenization and blending.
        a. Warm and blend the mixture while adding the high-purity oil.
        b. Once blended, cool to near room temperature and transfer into a sealable container.
13. Preparing Δ⁸-THC Dabbables:
  a. Exemplar 269—Dabbable oil/wax
    i. Add 30 mls of high-purity oil to a 60 ml disposable serum tube.
    ii. Add 20 mls of acetonitrile to the tube and secure the cap on the tube.
      1. Mix by shaking or using a vortex mixer.
    iii. Once mixed put mixture in the freezer over-night.
    iv. Separate acetonitrile from solid by carefully decanting or by pipetting into a syringe equipped with a 0.45μ chromatography filter.
    v. Filter the acetonitrile-high-purity oil mixture and then evaporate the acetonitrile outdoors in a well-ventilated area.
    vi. Once completely evaporated the wax can be scraped and transferred into a separate container.
      1. Cannabinoid terpene isolates and/or blended terpene profiles can be added to the wax.
        a. Terpenes added to wax while warm, stir to homogenize, cool and store in a silicon container or on a sheet wax paper.
14. Preparing Δ⁸-THC Vapes:
  a. Exemplar 270—Vapor (Flavored)
    i. Follow Steps I-VI for Exemplar 269, Preparing Δ⁸-THC Dabbables.
    ii. Warm high-purity wax obtained from the final step and add 5-10% v/v viscosity booster and homogenize.
      1. Temperature sustained at below boiling 212° F. (100° C.).
    iii. Add 5-10% terpenes or terpene isolates to the mixture and blend.
    iv. Heat the mixture for 2 minutes and blend, repeating this process 3 times.
    v. Transfer the vape liquid product into desired cartridges, pods or vaping devices.
      1. Use ceramic heating element technology with 1 mm intake holes or larger.

Figure 3:
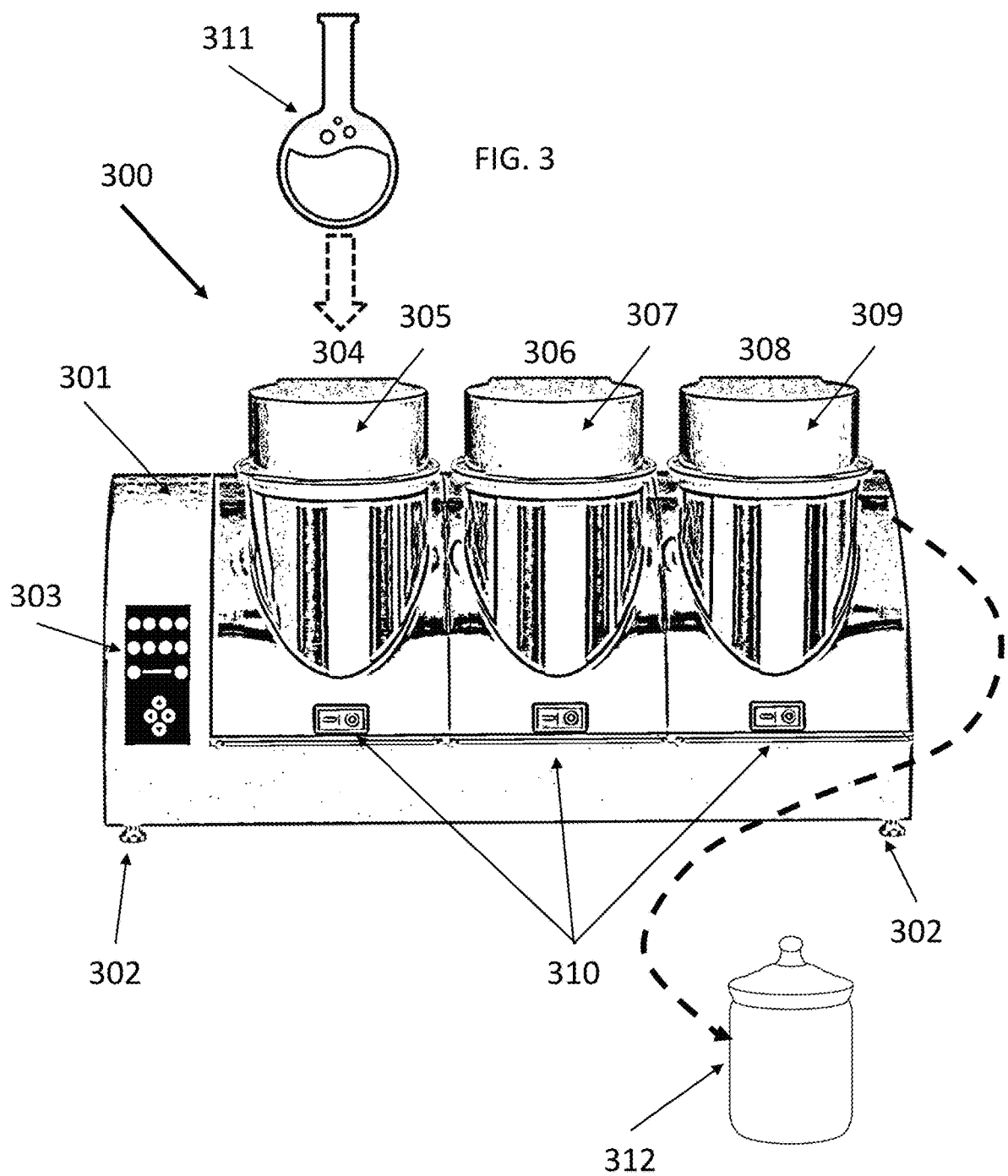
FIG. 3 is a diagram of the various components and assemblies and sub-assemblies comprising a home-based apparatus for catalyzing CBD to $\Delta^8$-THC.

Referring now to FIG. 3, a home-based apparatus for catalyzing CBD to Δ⁸-THC drawing on the methods described in Example 1 and Example 2 hereinabove is generally depicted by the numeral 300. The apparatus 300 generally consists of a housing 301 designed to fit on a typical kitchen countertop, utilizing adjustable protective feet 302. The housing 301 comprises multiple internal mechanisms described below (not shown) to facilitate the operation of the present general inventive concept. An electronic control panel 303 is electrically connected to an internal microcontroller (not shown), well known in the art, for the purposes of operating, controlling and timing the various automated features and functions of the apparatus. Three cylindrical chambers are provided as part of housing 301 including a reactor chamber 304, a quenching and liquid-liquid extraction chamber 306 and a titration and washing chamber 308. Each of said chambers 304, 306 and 308 are fitted with removable lids 305, 307 and 309 respectively. A travelling glass vessel, preferably a round-bottom flask 311, can be transferred from chamber to chamber by removing lids 305, 307 and 309. By incorporating three individual chambers 304, 306 and 308—each designed to perform a different function as part of the process described in detail hereinabove—the apparatus 300 can carry out dissimilar steps of the present general inventive concept simultaneously. Electrical activation switches 310 are provided so the user can enable or disable one or more of the chambers depending on which functions the apparatus 300 is performing at any given point in time. For example, a user may wish only to perform the reaction step in which case the switch for reaction chamber 304 would be 'on' and the switches for chambers 306 and 308 would be 'off'. Likewise, a user may wish to operate reaction chamber 304, while simultaneously operating quenching and liquid-liquid extraction chamber 306 and titration and washing chamber 308. In this example switches 310 for all three chambers 304, 306 and 308 would be 'on'. Any number of combinations and permutations of the various steps described in Example 1 hereinabove may be implemented simultaneously in this way.

Apparatus 300 is designed to be powered by a standard A.C. power cord (not shown) that provides all the electrical energy necessary for the apparatus to function as intended by the present general inventive concept. A three-prong, grounded power cord, well known in the art, is provided to permit safe operation of the machine when attached to a conventional A.C. wall outlet. A mains power switch is provided at the rear of the apparatus 300 (not shown) that permits interruption of electrical power when the machine is not in use.

The various chambers 304, 306 and 308 contain mechanisms such as magnetic stirrers, resistive heating elements, mechanical agitators, valves, sensors and the like (not shown) that are utilized in performing the various functions of the apparatus 300. For example, reaction chamber 304 incorporates a temperature controlled magnetic stirrer and heating mantle to thoroughly mix and react the starting material 120 inside of a glass vessel 311 when said vessel is inside chamber 304 and the chamber is switched 'on'. The control panel 303 in conjunction with the internal microcontroller (not shown) controls the various parameters needed to complete the reaction, to wit: the speed of the magnetic stirring, the temperature of the reactants inside the vessel, and the time required to complete the reaction. Audible and visual indicators that are part of control panel 303 alert the user when the various processes are complete.

Likewise, quenching and liquid-liquid extraction chamber 306 comprises a mechanical agitator to shake the mixture inside of the vessel 311 and valve mechanisms to provide outgassing of vessel 311 preventing an undesirable and potentially unsafe build-up of pressure within the vessel. Chamber 306 also includes various actuators and sensing means to provide for the separation of an organic layer from a aqueous layer as described in detail in Example 1 hereinabove. Chamber 306 is similarly controlled via control panel 303 and internal microcontroller (not shown) to produce the desired function of the present general inventive concept.

Finally titration and washing chamber 308 incorporates various actuators and sensing means to provide for the buffering and separation of the $\Delta^8$-THC infused oil from the salt solution as described in detail in Example 1 hereinabove. Again, in the same way chambers 304 and 306 are controlled, titration and washing chamber chamber 308 is automatically operated by said control panel 303 and internal microcontroller (not shown).

To operate apparatus 300, a home-based appliance for catalyzing CBD to $\Delta^8$-THC, the user would first initialize the machine by turning on the A.C. power and pressing the appropriate keys on control panel 303 to prepare the machine for use.

Next, the user would place the required reaction components in vessel 311 as described in detail in Example 1 hereinabove. Reaction chamber cap 305 would be removed from reaction chamber 304 and the vessel 311 placed inside. Chamber cap 305 would then be replaced to ensure safe operation of the machine. A safety interlock system (not shown) may optionally be employed to prevent operation of the machine in the event one or more of the chamber caps 305, 307 and 309 are not properly secured in place.

Once vessel 311 is secured inside reaction chamber 305, switch 310 for the reaction chamber is switched cony. The 'start' key is pressed on control panel 303 which instructs the internal microcontroller (not shown) to begin the reaction phase of the process. This function will continue until the material inside vessel 311 has completed catalyzation and is ready for quenching, at which time the visual and audible indicators associated with control panel 303 will alert the user. In addition, the apparatus 300 will automatically maintain the optimal conditions for the reaction products in vessel 311 in the event the user is unable to tend to the machine immediately after the reaction phase has been completed.

After the reaction phase has completed, the user would switch off reaction chamber switch 310, remove chamber cap 305 and remove vessel 311 from reaction chamber 304. Cap 307 of quenching and liquid-liquid extraction chamber 306 would subsequently be removed and vessel 311 would be transferred to chamber 306. Caps 305 and 307 would then be replaced and secured and the quenching and liquid-liquid extraction chamber activation switch 310 would be switched 'on'. The start button on control panel 303 would be pressed instructing the internal microcontroller (not shown) to begin the quenching and liquid-liquid extraction phase of the process as described in detail in Example 1 hereinabove. This function will likewise continue until the material inside vessel 311 has completed quenching and liquid-liquid extraction, at which time the visual and audible indicators associated with control panel 303 will again alert the user that the apparatus 300 is ready for the next step in the process.

Once the quenching and liquid-liquid extraction phase of the present general inventive concept has concluded, the user will switch off chamber 306 switch 310, remove chamber cap 307 and remove vessel 311 from chamber 306. Cap 309 of the titration and washing chamber 308 would subsequently be removed and vessel 311 would be transferred to titration and washing chamber 308. Caps 307 and 309 would then be replaced and secured and the titration and washing chamber 308 activation switch 310 would be switched 'on'. The start button on control panel 303 would be pressed instructing the internal microcontroller (not shown) to begin the titration and washing phase of the process as described in detail in Example 1 hereinabove. After completion of this phase, separated carrier oil infused with $\Delta^8$-THC will exit chamber 308 to a collection jar 312 which permits a convenient way to store the $\Delta^8$-THC infused oil for subsequent use.

In this way, the apparatus 300 of the present general inventive concept substantially automates the process of Example 1 described hereinabove. The high-level automation permits a user to safely operate the machine catalyzing CBD to a highly pure $\Delta^8$-THC. In addition to the functional controls, the apparatus of the present general inventive concept includes various alarm features to alert the user when a particular function cannot be completed. For example, if a problem is detected during the process, the unit will automatically stop and alert the user as to the apparatus' present 'trouble' condition. In all cases, where a problem is detected, the apparatus 300 has been designed to fail-safe and prevent injury that might occur from continued operation in the alarm state. These design elements of the present general inventive concept are intended to permit the safe automated operation of the apparatus in a home environment, for example a home kitchen.

Once the apparatus 300 has completed all three phases of operation, the output material 160 consisting of a carrier-oil infused with $\Delta^8$-THC, can be used in producing myriad compositions for personal consumption as described in Example 2 hereinabove. The versatility of the apparatus 300 is such that the ease-of-use and reduced cost of producing these consumables will make apparatus 300 of the present general inventive concept a very attractive commercial offering.

While the preferred embodiments of the present general inventive concept have been described above, it will be recognized and understood that various modifications may be made therein, and the appended claims are intended to cover all such modifications which may fall within the spirit and scope of the invention.

What is claimed is:

1. A method of converting CBD to a tetrahydrocannabinol, comprising the steps of:
    obtaining a pure CBD isolate;
    cooling said CBD isolate to a first predetermined temperature to prevent degradation thereof;
    preparing a mixture of catalyst and food grade oil, wherein said catalyst is present in an amount of 0.0001-0.2000 mole fractions per X moles of said isolate, said mixture is disposed in a container purged with an inert gas and cooled to a second predetermined temperature within at least a temperature degree range of said first predetermined temperature to prevent degradation thereof;
    adding the cooled mixture and isolate to a reaction vessel while providing continuous stirring of the mixture therein;
    providing a condensing apparatus in sealable communication with said reaction vessel;
    submerging said reaction vessel in a thermally predetermined environment to warm to a third predetermined temperature as a function of said food grade oil's thermal transition point;
    after a predetermined time of mixing said mixture, said vessel is emerged into ambient room temperature;
    quenching said mixture; and
    transferring said quenched mixture to a separatory apparatus to provide an emulsion whereby separable layers form containing an organic oil layer material containing $\Delta^8$-THC with a purity of at least 85%.

2. The method of converting CBD to a tetrahydrocannabinol of claim 1, which further includes the step of obtaining said organic oil layer material and adding a terpene thereto.

3. The method of converting CBD to a tetrahydrocannabinol of claim 1, which further includes the step of obtaining said organic oil layer material and placing into a distillation apparatus and distilling to collect desired fractional material.

4. The method of converting CBD to a tetrahydrocannabinol of claim 1, which further includes the step of obtaining said organic oil layer material and placing into a vessel with an organic solvent and operably connecting a condensing and vacuum apparatus thereto, and stirring these at a temperature to precipitate the isolate to provide an organic crystal material.

5. The method of converting CBD to a tetrahydrocannabinol of claim 1, which further includes the step of obtaining said organic oil layer material and providing into a vessel with a solvent, warming to dissolve said organic oil layer material, then cooling to provide crystals, and removing solvent.

6. The method of converting CBD to a tetrahydrocannabinol of claim 1, which further includes the step of obtaining said organic oil layer material and providing into a vessel with an eluent, adding said organic oil layer material to a column for column chromatography.

7. The method of converting CBD to a tetrahydrocannabinol of claim 1, wherein said quenching is performed by initial cooling said reaction mixture further in an ice bath (−15° C.-0° C.) to precipitate crystals from the recoverable catalyst and filter using vacuum filtration, wherein said crystals are rinsed with cold solvent, and a filtrant is taken and then quenched in distilled water, wherein said quenched mixture is stirred magnetically for a predetermined period.

8. The method of converting CBD to a tetrahydrocannabinol of claim 1, wherein said quenching is performed by pouring said reaction mixture directly into distilled water while stirring magnetically, and stirring magnetically for a predetermined period.

9. The method of converting CBD to a tetrahydrocannabinol of claim 1, wherein said quenching is performed by pouring said reaction mixture directly into saturated solution of a base and allow to stir magnetically for a predetermined period and wherein said mixture is heated after pouring into said base, then cooled again to room temperature and separated by layer.

10. The method of converting CBD to a tetrahydrocannabinol of claim 1, wherein said organic oil layer material is provided in one of a wax, a sap, a distillate, an isolate, and a crystalline form.

11. A method processing Hemp biomass for conversion to $\Delta^8$-THC, which includes the steps of:
    (a) obtaining dried post-harvest Hemp floral biomass to obtain a water content below 15% prior to milling;
    (b) milling said Hemp floral biomass into a uniform particle size;
    (c) decarboxylating said Hemp floral biomass in an oven that is set in a range of a predetermined temperatures 70-115° C. and for a predetermined range of time period, the material is generally decarboxylated for 0.25 h-1 h;
    (d) extracting crude oil;
    (f) winterizing said crude oil to provide waxes;
    (g) removing solvent from said winterized waxes to provide pure CBD distillate; and
    (h) dewaxing said distillate to provide an isolate oil and crystallizing isolate oil to provide crystalline isolate having a total THC content less than a predetermined % of less than about 0.3%.

12. The method processing Hemp biomass for conversion to $\Delta^8$-THC of claim 11, wherein said milling uses a cryo-miller ranging from 0-4 mm mill sizing.

13. The method processing Hemp biomass for conversion to $\Delta^8$-THC of claim 11, wherein said extraction of crude oil is performed by supercritical CO2 extraction.

14. The method processing Hemp biomass for conversion to $\Delta^8$-THC of claim 11, wherein said predetermined temperatures range from 70-105° C.

15. The method processing Hemp biomass for conversion to $\Delta^8$-THC of claim 11, wherein said predetermined time period ranges from 0.25 h-1 h.

16. The method processing Hemp biomass for conversion to $\Delta^8$-THC of claim 11, wherein said winterization occurs in at one of alcohols and non-polar organic solvents by warming said crude oil and stirring into said at least one said solvent until fully dissolved, and cooling to −20° C.-0° C. to precipitate out said waxes, wherein said waxes are collected via vacuum filtration.

17. The method processing Hemp biomass for conversion to $\Delta^8$-THC of claim 16, wherein said winterized waxes are added to a rotary evaporator to further reduce the solvent that was used in the winterization step.

18. The method processing Hemp biomass for conversion to $\Delta^8$-THC of claim 11, which further includes the steps of:
(g) obtaining said crystalline isolate;
(h) cooling said crystalline isolate to a predetermined temperature to prevent degradation thereof;
(i) preparing a mixture of catalyst and food grade oil, wherein said catalyst is present in an amount of 0.0001-0.2000 mole fractions per X moles of said crystalline isolate, said mixture is disposed in a container purged with an inert gas and cooled to a second predetermined temperature within at least a temperature degree range of said first predetermined temperature to prevent degradation thereof;
(j) adding the cooled mixture and said isolate oil crystal slurry to a reaction vessel while providing continuous stirring of the mixture therein;
(k) providing a condensing apparatus in sealable communication with said reaction vessel;
(l) submerging said reaction vessel in a thermally predetermined environment to warm to a third predetermined temperature as a function of said food grade oil's thermal transition point;
(m) after a predetermined time of mixing said mixture, said vessel is emerged into ambient room temperature;
(n) quenching said mixture; and
(o) transferring said quenched mixture to a separatory apparatus to provide an emulsion whereby separable layers form containing an organic oil layer material containing $\Delta^8$-THC with a purity of at least 85%.

* * * * *